Feb. 3, 1959 L. B. DYMOND Plant Pat. 1,806
PEAR TREE
Filed April 7, 1958
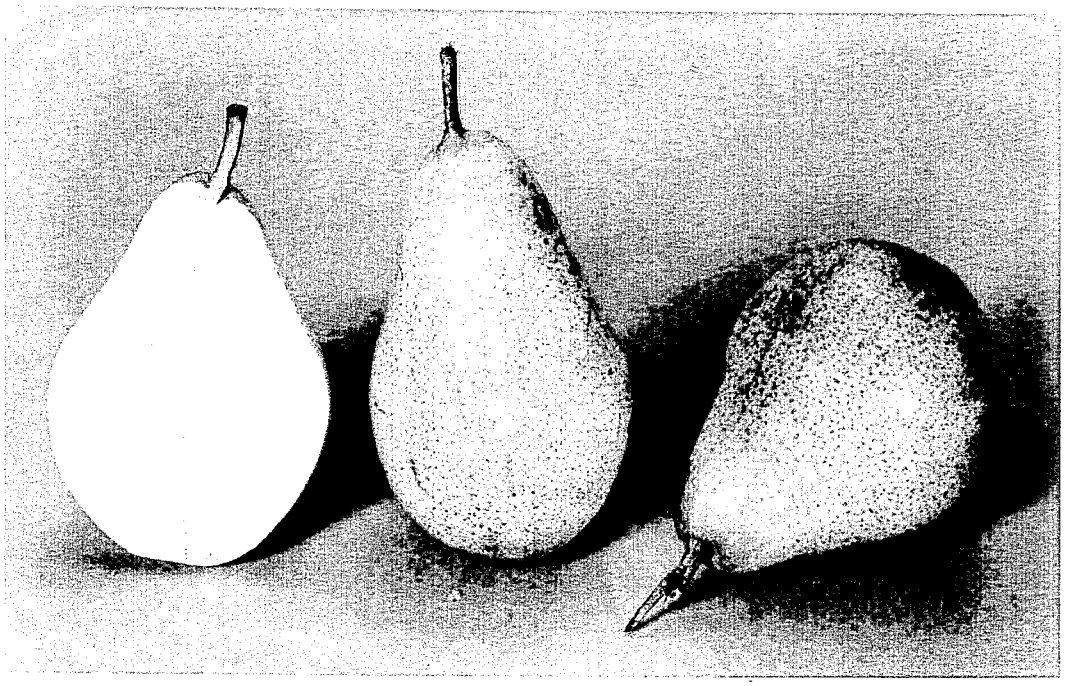
INVENTOR
L. B. Dymond
BY Robb & Robb
ATTORNEYS United States Patent Office Plant Pat. 1,806

Patented Feb. 3, 1959

1,806

PEAR TREE

Lawrence B. Dymond, Tunkhannock, Pa., assignor to Kelly Brothers Nurseries, Inc., Dansville, N. Y., a corporation of New York Application April 7, 1958, Serial No. 727,013

1 Claim. (Cl. 47—62)

The present invention relates to a new and distinct variety of pear tree which was discovered by me as a newly found seedling on my cultivated property at Tunkhannock, Pennsylvania.

At the time of my discovery, my attention was attracted to the new variety while clearing off a lot which was a part of my farm at Tunkhannock, Pennsylvania. At that time, the tree had attained a growth so that its trunk was about three inches in diameter, and it drew my attention primarily because of the enormous size of the fruit borne on the tree. I thereupon took steps to preserve the tree, keep it under observation, and to later have it asexually reproduced on my behalf. These observations, as well as the asexual reproductions, performed at Aspers, Pennsylvania by budding, conclusively established that the new variety was characterized by the consistently large size of the fruit, among other features which form a unique and distinct combination different from any other pear variety of which I am aware, said combination including the following predominant characteristics:

(1) Attractive dark foliage;

(2) Heavy fruit-bearing habit;

(3) Good flavor and good keeping quality of the fruit;

(4) Large and uniform size of the fruit, with a fruit color very similar to that of the Bartlett variety (unpatented); and (5) A fruit-ripening habit averaging about 10 days later than that of the Bartlett variety.

While the actual parentage of my new variety is not known, it is definitely distinct from the Bartlett variety and from all other varieties of this type, thereby making it particularly valuable from a commercial standpoint.

The accompanying drawing shows typical fruit specimens of the new variety as depicted in color as nearly true as it is reasonably possible to make the same in a color illustration of this character, with one of the fruit specimens being shown in cross-section.

The following is a detailed description of my new variety, with color terminology in accordance with general color terms of ordinary dictionary significance:

(Observations made from specimens grown at Tunkhannock, Wyoming County, Pennsylvania.)

Dates first and last pickings: About September 7th—about September 14th, respectively.

Tree: Medium size; vigorous; upright; tall; vase-formed; rapid-growing; hardy; productive; regular bearer.

*Trunk.*—Stocky; medium smoothness.

*Branches.*—Medium thickness; medium smoothness. Color — brownish-gray. Lenticles — medium number; small.

*Leaves.*—Medium size; medium length (about 2⅝ inches); wide (about 1⅞ inches); oval; abruptly pointed; medium thickness; smooth. Color—an attractive green color somewhat darker than that of the Bartlett variety. Margin—finely serrate. Petiole—slender; long (from about 1⅝ inches to 2 inches).

Flowers: Medium blooming period as compared with other varieties; self-pollinating.

*Dates of first and full bloom.*—About May 5th—about May 10th, respectively.

*Size.*—Medium.

*Color.*—White.

Fruit:

*Maturity when described.*—Between September 10th and September 15th.

*Size.*—Uniform; large. Axial diameter—from about 3 inches to 3½ inches. Transverse diameter—from about 2½ inches to 2¾ inches.

*Form.*—Variable, but usually symmetrical; regular shape; substantially pyriform, with medium neck.

*Cavity.*—Symmetrical; flaring; undulate; lipped. Depth—shallow. Breadth—broad.

*Markings.*—Slight russet.

*Basin.*—Unsymmetrical; rounded; angular; crowned; glabrous.

*Stem.*—Medium stout; bracts wanting; length about 1¼ inches.

*Calyx.* — Open. Segments — persistent; broadly acute; length from about 1/16 inch to ⅛ inch; erect; with outer and inner surfaces pubescent.

*Eye.*—Medium size; open.

*Skin.*—Thick; tough; rough. Dots—obscure; many; small; even; circular. Color—brown; distribution—numerous at calyx, but less at stem end. Ground color — yellow. Color markings—splashed and blushed.

*Bloom.*—Wanting.

*Scarfskin.*—Wanting.

*General color effect.*—Yellow, with pink blushed cheek.

*Flesh.*—Juicy. Color—white, with yellowish tint. Texture—firm; tender; melting. Flavor—subacid; sprightly. Quality—good.

*Core.*—Median. Bundle area—large. Halves of core—equal. Bundles: color—yellowish; alternate bundle—reaches calyx tube below stamens. Core lines—meeting; indistinct in cross section. Carpellary area—distinct; small. Calyx tube—pubescent; broadly urn-shaped; depth of tube to shoulder—about 3/16 inch; entire depth—about ⅜ inch. Styles — wanting. Stamens — distinct. Axillary cavity — wanting. Seed cells — axile; closed; cell walls—thick; length—about ⅜ inch; breadth—about ¼ inch. Longitudinal section—narrowly ovate; surface smooth; cross section broad.

Seeds: Usually from 4 to 6, but sometimes only 1 or none.

Use: Market; local; culinary.

Keeping quality: Good; from 4 to 8 weeks in ordinary storage.

Disease resistance: No evidence of blight or scab during prolonged observations, as compared with other varieties grown under comparable cultural conditions at Tunkhannock, Pennsylvania.

I claim:

A new and distinct variety of pear tree, substantially as herein shown and described, characterized particularly as to novelty by the unique combination of attractive dark foliage, a heavy fruit-bearing habit, good flavor and good keeping quality of the fruit, large and uniform size of the fruit, with a fruit color very similar to that of the Bartlett variety (unpatented), and a ripening habit of the fruit averaging about 10 days later than the ripening period of the Bartlett variety.

References Cited in the file of this patent

Publication: "The Pears of New York" by Hedrick, published by the New York Agricultural Experiment Station, 1921.